United States Patent [19]

Hardwick et al.

[11] Patent Number: 4,648,868
[45] Date of Patent: Mar. 10, 1987

[54] APPARATUS FOR CONTROLLING FLOW AND PRESSURE MEASUREMENT

[75] Inventors: Martha K. Hardwick, Tustin; Kelly A. Pike, Laguna Hills; George D. Evans, II, Arlington; Ronald Edwards, San Clemente; Jacob J. Norman, Westminster, all of Calif.

[73] Assignee: American Hospital Supply Corporation, Evanston, Ill.

[21] Appl. No.: 782,032

[22] Filed: Sep. 30, 1985

[51] Int. Cl.⁴ .................... A61B 5/02; F16K 21/00
[52] U.S. Cl. ......................... 604/32; 604/248; 128/675; 137/625.17; 251/208
[58] Field of Search ............ 604/118, 32, 248, 52, 604/250, 249, 33; 128/675, 672, 673, 674, 748, DIG. 12; 137/625.17; 251/208

[56] References Cited

U.S. PATENT DOCUMENTS

| | | |
|---|---|---|
| 1,101,868 | 6/1914 | McCoy . |
| 1,888,207 | 11/1932 | Bard . |
| 1,948,062 | 2/1934 | Brunette ................ 251/137 |
| 2,035,762 | 3/1936 | Roberts ................. 251/164 |
| 2,150,198 | 3/1939 | Werneman ............. 251/112 |
| 3,157,201 | 11/1964 | Littmann ............... 128/675 |
| 3,418,853 | 12/1968 | Curtis . |
| 3,565,056 | 2/1971 | Statham . |
| 3,603,347 | 9/1971 | Paolini ................. 137/625.17 |
| 3,610,228 | 10/1971 | Temkin . |
| 3,720,233 | 3/1973 | Shur et al. ............ 137/625.17 |
| 3,834,372 | 9/1974 | Turney . |
| 3,899,766 | 8/1975 | Mermelstein . |
| 4,012,940 | 3/1977 | Change et al. . |
| 4,063,553 | 12/1977 | Karsh ................... 128/675 |
| 4,072,056 | 2/1978 | Lee . |
| 4,185,641 | 1/1980 | Minior et al. . |
| 4,192,303 | 3/1980 | Young et al. . |
| 4,210,178 | 7/1980 | Morse et al. . |
| 4,226,124 | 10/1980 | Kersten . |
| 4,227,420 | 10/1980 | Lamadrid . |
| 4,252,126 | 2/1981 | Mandl . |
| 4,261,208 | 4/1981 | Hok et al. . |
| 4,291,702 | 9/1981 | Cole . |
| 4,300,571 | 11/1981 | Waldbillig . |
| 4,327,350 | 4/1982 | Erichsen . |
| 4,335,729 | 6/1982 | Reynolds et al. . |
| 4,341,224 | 7/1982 | Stevens . |
| 4,365,635 | 12/1982 | Bowman . |
| 4,368,575 | 1/1983 | Erichsen et al. . |
| 4,545,389 | 10/1985 | Schaberg et al. ....... 128/675 |

OTHER PUBLICATIONS

Comprehensible Intracranial Pressure Evaluation and Relief System (CIPER TM) booklet, Medex Inc., 3637 Lancon Rd., Hilliard, OH 43026, 1983.

Primary Examiner—C. Fred Rosenbaum
Assistant Examiner—John D. Ferros
Attorney, Agent, or Firm—Gordon L. Peterson

[57] ABSTRACT

An apparatus comprising a valve body having first, second and vent ports and a generally tubular valve element having a peripheral wall with first, second and vent openings in the peripheral wall leading to the interior of the tubular valve element. The valve element is mounted in the valve body for rotational movement between first and second rotational positions and for axial movement between first and second axial positions. A pressure sensor is exposed to the fluid pressure within the valve body. In the first rotational position of the valve element, drip flow is provided between the first and second ports, and in the second rotational position, the vent port is open to provide communication between the pressure sensor and the atmosphere. To provide flush flow between the first and second ports, the valve element is moved to the second axial position.

19 Claims, 7 Drawing Figures

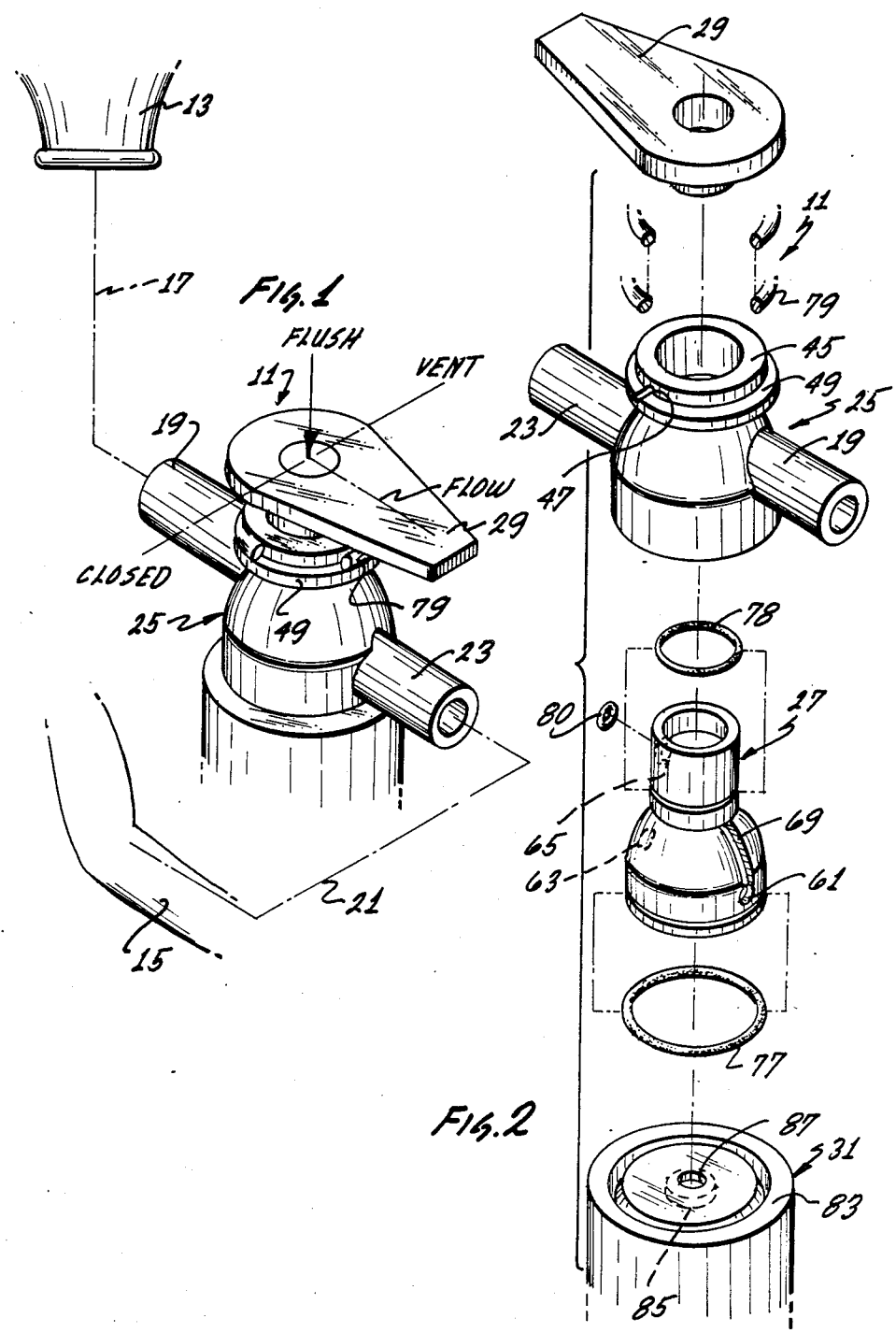

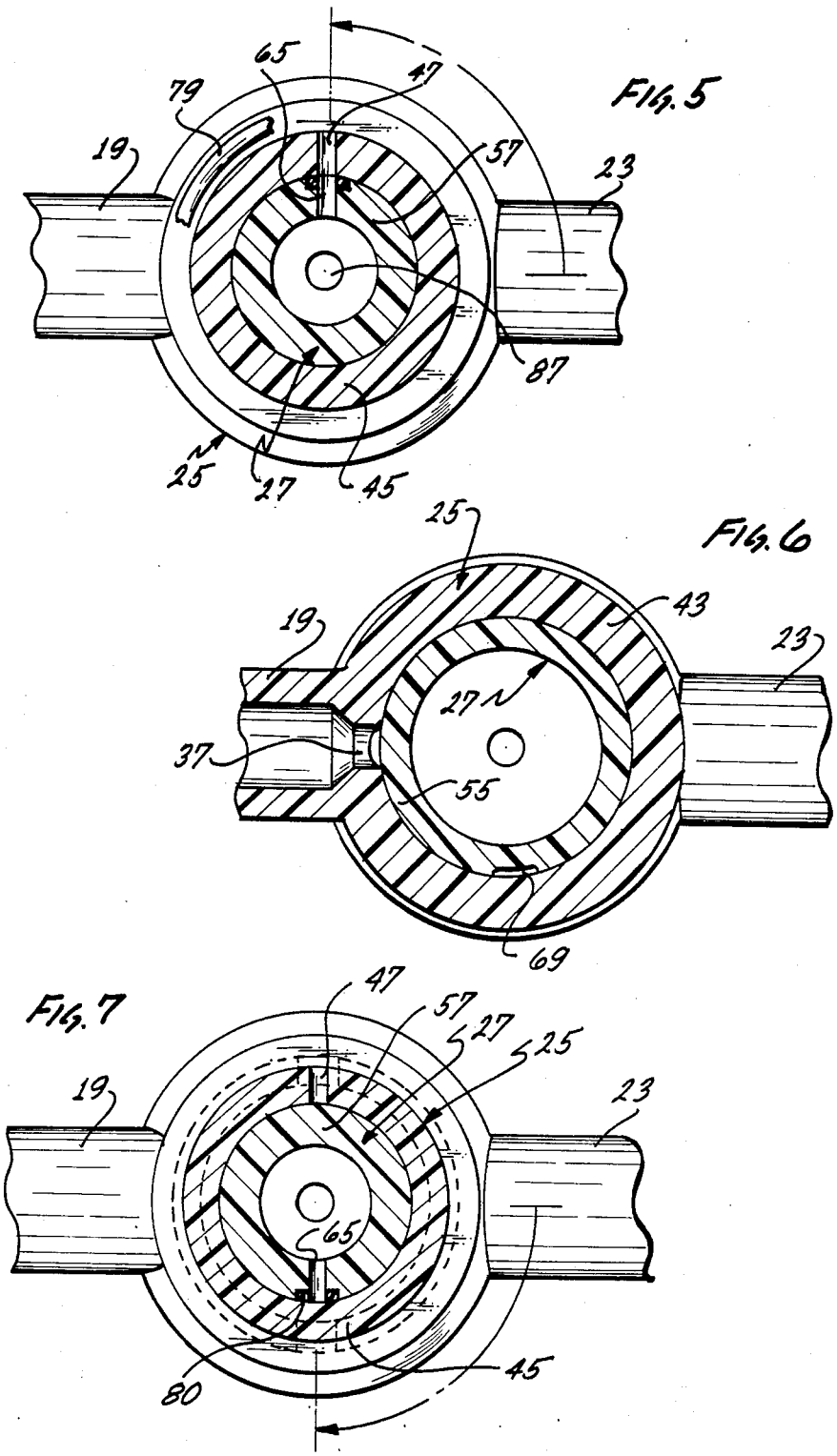

APPARATUS FOR CONTROLLING FLOW AND PRESSURE MEASUREMENT

BACKGROUND OF THE INVENTION

Various medical procedures involve the infusion of a liquid into the patient and the measurement of blood pressure. For example, in the intravenous administration of a liquid, the desired liquid is transmitted from a bag or other container through flexible tubing and a needle to the vein of a patient. Flow control of the liquid can be obtained by various components, including separate stop cocks and flush valves, and a separate pressure transducer may be employed to measure blood pressure.

The use of separate individual components for controlling liquid flow through the tubing to the patient adds to the complexity of the system. In addition, the separate components make operation of the system more difficult and may tend to increase the likelihood of operator error.

The flow control function may require a capability for restricted or drip flow, flush or high-volume flow, no flow, and venting. Drip flow may be required for, among other things, to prevent occlusion of the needle or other instrument inserted into the patient. High volume or flush flow may be required, for example, to flush bubbles from the system or to clean the tubing and connected components. The vent mode is usable, for example, for calibrating pressure sensing equipment. Although these modes of operation could be provided as four different rotational positions of a rotary valve, the valve may have to be larger than desired in order to provide these four positions with appropriate seals and orifice sizes. Also, a rotary valve of this type may not permit fail safe operation in which the valve cannot unintentionally be left in the flushing position.

SUMMARY OF THE INVENTION

This invention solves these problems by providing a single apparatus which performs the functions of both a stop cock and a flush valve. In addition, the pressure-sensing function can be accomplished with the same apparatus. The apparatus, which may be of simple, lightweight construction and constructed in small sizes, has a fail-safe feature which prevents it from being left in the flush position.

The invention may be embodied in an apparatus which includes a valve body having a chamber and first and second ports and a valve element mounted at least partially in the chamber for rotational movement relative to the valve body between first and second rotational positions. To reduce the number of rotational positions required to obtain the flow-control functions desired, the valve element is also mounted for axial movement relative to the valve body between first and second axial positions.

The valve element and the valve body cooperate to define a flow passage extending between the first and second ports. The flow passage provides different flow characteristics in the first rotational position than in the second rotational position when the valve element is in said first axial position. For example, the different flow characteristics may be on, i.e., some flow, off or no flow, restricted flow or venting of the flow passage.

One common requirement is for drip flow, and to provide for this, at least a portion of the flow passage is of relatively restricted cross-sectional area when the valve element is in the first rotational position and the first axial position. To obtain a relatively high volume or flushing flow, the valve element is retained at the first rotational position but moved to the second axial position. Preferably, flush flow results whenever the valve element is in the second axial position regardless of its rotational position. This could open a large cross-sectional area bypass passage around the restricted portion of the flow passage and/or greatly enlarge the cross-sectional area of the restricted portion of the flow passage. Preferably, a flush-flow passage is provided between the valve element and the valve body which extends circumferentially of the valve element. To prevent unintended retention of the valve element in the flushing position, i.e., the second axial position, the apparatus preferably includes resilient means for urging the valve element toward the first axial position.

The housing preferably includes a vent port adapted to communicate with the atmosphere, and the valve element blocks communication between the vent port and the flow passage in the first rotational position of the valve element. However, in the second rotational position of the valve element, the valve element provides communication between the vent port and the flow passage. This is useful, for example, in calibrating or zeroing any pressure sensor that is exposed to the fluid pressure in the flow passage. To enable the venting function to occur, preferably the flow passage between the first and second ports is closed by the valve element in the second rotational position of the valve element. If desired, the valve element may also have a third rotational position in which the flow passage is closed, and communication between the vent port and the flow passage is blocked.

The invention, together with additional features and advantages thereof, may best be understood by reference to the following description taken in connection with the accompanying illustrative drawing.

BRIEF DESCRIPTION OF THE DRAWING

FIG. 1 is an isometric view showing an apparatus constructed in accordance with the teachings of this invention being used as one of the control elements for controlling the administration of a saline solution to a patient.

FIG. 2 is an exploded isometric view of the apparatus.

FIGS. 5 and 6 are sectional views taken generally along lines 5—5 and 6—6, respectively, of FIG. 3 with the valve element turned to the second rotational position.

FIG. 7 is a sectional view similar to FIG. 5 illustrating the third rotational position of the apparatus with all the ports closed.

DESCRIPTION OF THE PREFERRED EMBODIMENT

Figure 3:
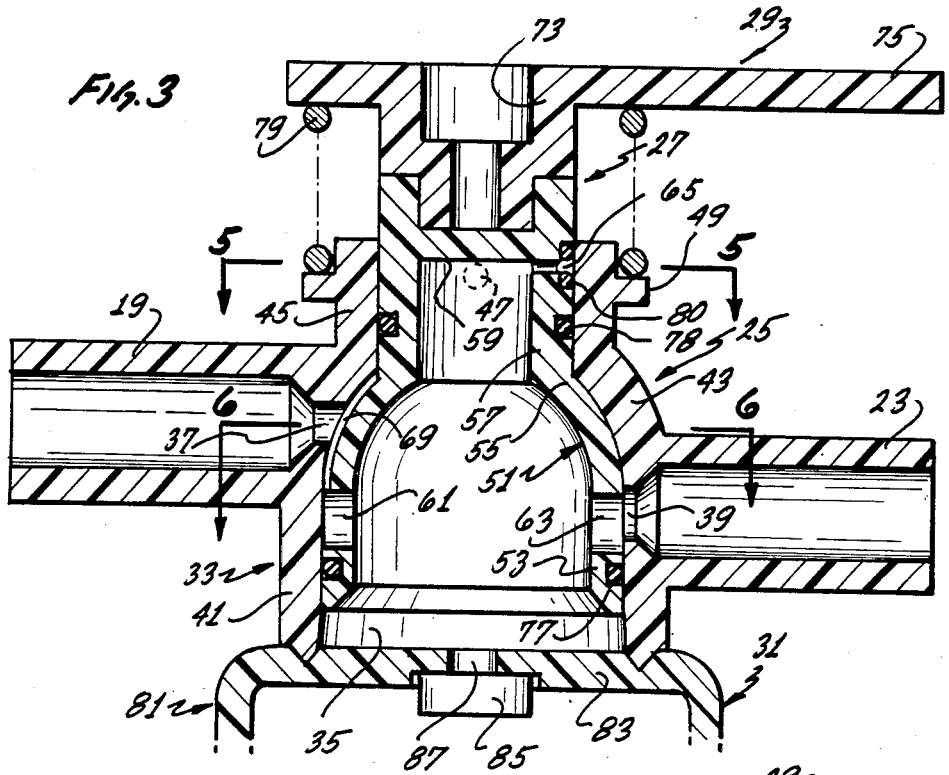
FIG. 3 is a longitudinal, sectional view through the apparatus with the valve element at the first rotational position and the first axial position to provide drip flow through the apparatus.

FIG. 1 shows an apparatus 11 constructed in accordance with the teachings of this invention interposed between a source of liquid, such as a saline bag 13 and a patient 15. Tubing 17 joins the saline solution bag 13 to an inlet fitting 19, and tubing 21 joins an outlet fitting 23 of the apparatus 11 to the patient 15. Of course, other components may also be interposed in the tubing 17 and 21, and the apparatus 11 is usable with many different systems.

The apparatus 11 includes a valve body 25, a valve element 27, and an operating handle 29. The apparatus 11 may optionally include a transducer 31 coupled to the valve body 25. The valve body 25, the valve element 27 and the handle 29 may each be molded of a suitable plastic material.

The valve body 25 includes a peripheral wall 33 (FIG. 3) defining a chamber 35. The valve body 25 also includes the fittings 19 and 23 which are integral with the peripheral wall 33 and which are axially offset, with the fitting 23 being below (as viewed in FIG. 3) the fitting 19. The valve body 25 has an inlet port 37 and an outlet port 39 at the fittings 19 and 23, respectively, which are axially offset and spaced apart 180 degrees circumferentially. Although the peripheral wall 33 could be of different configurations, in the embodiment illustrated, it has a cylindrical section 41, a dome or part spherical section 43, and a cylindrical section 45.

A vent port 47 is provided in the cylindrical section 45 of the peripheral wall 33, and a peripheral flange 49 surrounds the cylindrical section 45. The vent port 47 is displaced 90 degrees from the ports 37 and 39.

The valve element 27 has a peripheral wall 51, with a cylindrical section 53, a part-spherical or dome section, 55, and a cylindrical section 57. The valve element 27 is tubular, and the upper end of the valve element is closed by a web 59 which is spaced downwardly (as viewed in FIG. 3) from the upper end of the peripheral wall 51. The lower end of the valve element is open.

The peripheral wall 51 has an inlet opening 61 and an outlet opening 63 formed in the cylindrical section 53 and a vent opening 65 in the cylindrical section 57. The openings 61 and 63 are diametrically opposed, and the vent opening 65 is displaced 90 degrees from the openings 61 and 63. A drip groove 69 is formed in the outer surface of the dome section 55 and extends for the full axial length of the dome section and into the cylindrical section 53.

The peripheral walls 33 and 51 are of similar geometric configuration, and the valve element 27 is sized to be received within the chamber 35 for axial and rotational movement. In the position shown in FIG. 3, the lower end of the valve element 27 is above the lower end of the valve body 25, and the upper end of the valve element projects out of the valve body 25.

The operating handle 29 includes a stepped shaft 73 and an arm 75 which can be manually grasped. The shaft 73 is partially received within the cylindrical section 57 of the peripheral wall 51 and seats against the web 59. The operating handle 29 can be suitably affixed, as by ultrasonic welding, to the peripheral wall 51 so that it can rotate the valve element 27. A coil compression spring 79 acts between the flange 49 and the handle 29 to resiliently bias the handle 29 and the valve element 27 to the position shown in FIG. 3. Annular seals 77, 78 and 80 seal the interface between cylindrical sections 41 and 53, cylindrical sections 45 and 57, and around the vent opening 65, respectively.

The transducer 31 includes a transducer housing 81 which is joined to the valve body 25, as by ultrasonic welding, to form with the valve body a housing for the apparatus. The housing 81 has an end wall 83 which is bonded to the peripheral wall 33 and which closes the lower end of the chamber 35. A pressure sensor 85 is carried by the wall 83 and is exposed to the pressure in the chamber 35 through a port 87 in the end wall.

The valve element 27 has three rotational positions and two axial positions, and in FIG. 3, the valve element is in the first rotational position and the first axial position. In the position of FIG. 3, the opening 63 is in registry with the outlet port 39, and the groove 69 extends from the inlet port 37 to the opening 61. More specifically, the groove 69 confronts a region of the peripheral wall 33 along the dome section 43 and the cylindrical section 41 to define a restricted passage. Accordingly, saline solution from the bag 13 can flow through the tubing 17, the inlet port 37, and a flow passage comprising a region of the groove 69, the opening 61, the chamber 35 and the opening 63 to the outlet port 39. The flow rate is controlled by the restricted cross-sectional area of the groove 69 between the inlet port 37 and the opening 61. For example, the flow rate may be a drip flow rate. During the time that drip flow occurs, the pressure sensor 85 can sense the pressure of the fluid in the chamber 35, and because this fluid is in contact with the blood, the blood pressure can be measured.

Figure 4:
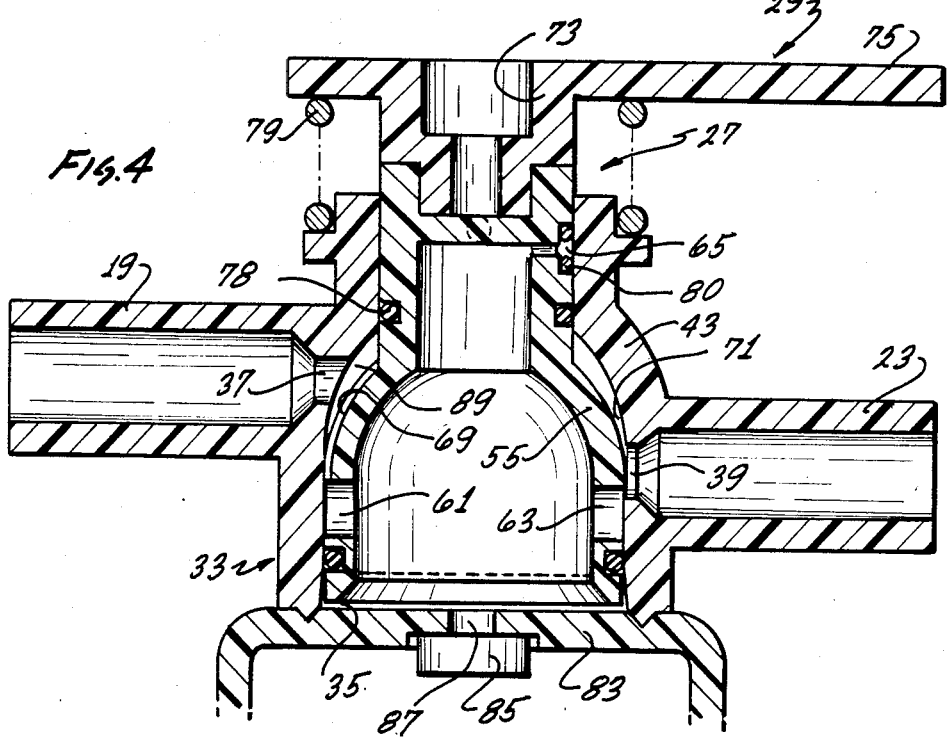
FIG. 4 is a view similar to FIG. 3 with the valve element in the flush position.

To obtain a relatively high-volume flush flow, the operator pushes the handle 29 downwardly against the biasing action of the spring 79 to the second axial position shown in FIG. 4. This separates the sloping dome sections 43 and 55 to provide an annular region or flush passage 89 within the chamber 35 between the valve element 27 and the valve body 29 of relatively large cross-sectional area. The annular region 89 extends from the inlet 37 all the way to the outlet port 39 so that the resulting flow passage from the inlet port 37 to the outlet port 39 is of larger cross-sectional area and much less restricted than the flow passage in the position of FIG. 3. Accordingly, a high volume or flush flow can take place through the apparatus 11. In the positions of FIGS. 3 and 4, the cylindrical section 57 of the valve element 27 confronts and blocks off the vent port 47 from the chamber 35.

The valve element 27 can be rotated 90 degrees counterclockwise as viewed in FIG. 5 to a second rotational position in which the vent opening 65 is in registry with the vent port 47 FIG. 5), and the groove 69 is circumferentially spaced 90 degrees from the ports 37 and 39 (FIG. 6) so that the peripheral wall 51 of the valve element 27 closes off the ports 37 and 39. In the position of FIGS. 5 and 6, the chamber 35 and the interior of the valve element 27 are exposed to atmospheric pressure through the vent opening 65 and the vent port 47. Thus, the pressure sensor 85 is likewise exposed to atmospheric pressure so that it can be calibrated or zeroed.

The valve element 27 can also be rotated 90 degrees clockwise from the position of FIG. 3 to a closed position shown in FIG. 7. In the closed position, the vent opening 65 is closed by a confronting region of the cylindrical section 57, and the groove 69 is displaced from the ports 37 and 39 to enable the peripheral wall 51 to close off the ports 37 and 39. Thus, in the closed position, the ports 37, 39 and 47 are all closed.

Although an exemplary embodiment of the invention has been shown and described, many changes, modifications and substitutions may be made by one having ordinary skill in the art without necessarily departing from the spirit and scope of this invention.

We claim:

1. An apparatus comprising:

a valve body having a chamber and first and second ports communicating with said chamber;

a valve element mounted at least partially in the chamber of the valve body for rotational movement relative to the valve body between first and second rotational positions and for axial movement relative to the valve body between first and second axial positions;

said valve element and said valve body cooperating to define a flow passage between said ports which provides different flow characteristics in the first rotational position than in the second rotational position when the valve element is in said first axial position; and means responsive to movement of the valve element to the second axial position at least when the valve element is at the first rotational position for providing for flush flow through said chamber and between said ports with the flush flow being greater than the flow in either of said rotational positions with the valve element in said first axial position.

2. An apparatus as defined in claim 1 wherein at least one of the first and second ports is closed by the valve element in said second rotational position.

3. An apparatus as defined in claim 1 including a pressure sensor exposed to the fluid pressure within said flow passage.

4. An apparatus as defined in claim 1 wherein said flush flow means is responsive to movement of the valve element to said second axial position when the valve element is in either of said first and second rotational positions for providing said flush flow.

5. An apparatus as defined in claim 1 wherein said flush flow means is responsive to movement of the valve element to said second axial position at least when the valve element is in said first rotational position to provide a flush flow passage between the valve element and the valve body and said flush flow passage extending circumferentially of the valve element.

6. An apparatus as defined in claim 1 wherein the valve body has a vent port adapted to communicate with the atmosphere and said apparatus includes means responsive to the valve element being in the first rotational position for blocking communication between the vent port and the flow passage and means responsive to the valve element being in the second rotational position and said one axial position for providing communication between the vent port and the chamber and said first-mentioned providing means includes means for closing at least one of the first and second ports to terminate flow between said first and second ports, and said apparatus includes means responsive to the valve element being in said second rotational position and at said first axial position for closing said first and second ports.

7. An apparatus comprising:

a valve body having a chamber and first and second ports communicating with said chamber;

a valve element mounted at least partially in the chamber of the valve body for rotational movement relative to the valve body between first and second rotational positions and for axial movement relative to the valve body between first and second axial positions;

means defining a flow passage between said first and second ports with at least a portion of the flow passage being of relatively restricted cross-sectional area when the valve element is in said first rotational position and said first axial position whereby the flow passage can provide restricted flow between the first and second ports;

means responsive to movement of the valve element to the second axial position at least when the valve element is at the first rotational position for greatly enlarging the cross-sectional area of the flow passage whereby the flow passage can accommodate flush flow; and means responsive to the valve element being in the second rotational position and said first axial position for providing a flow characteristic in said flow passage which is different from said restricted flow.

8. An apparatus as defined in claim 7 wherein the valve body has a vent port adapted to communicate with the atmosphere and said apparatus includes means responsive to the valve element being in the first rotational position for blocking communication between the vent port and the flow passage and means responsive to the valve element being in the second rotational position and said one axial position for providing communication between the vent port and the chamber and said first-mentioned providing means includes means for closing at least one of the first and second ports to terminate flow between said first and second ports.

9. An apparatus as defined in claim 8 including a pressure sensor exposed to the fluid pressure within said flow passage.

10. An apparatus as defined in claim 7 including a pressure sensor exposed to the fluid pressure within said flow passage.

11. An apparatus as defined in claim 8 wherein the valve element is rotatable relative to the valve body to a third rotational position in which the vent port and at least one of the first and second ports is closed.

12. An apparatus as defined in claim 7 wherein said portion of the flow passage includes a groove in the valve element and at least a portion of said groove confronts the first port in the first rotational position at the first axial position.

13. An apparatus as defined in claim 12 wherein the valve element has first and second peripheral wall segments which confront the first and second ports, respectively, in the first rotational position and the first axial position, first and second openings in the first and second peripheral segments, respectively, with the region between the first and second openings being open for the passage of fluid therebetween and said groove is formed in one of the peripheral wall segments whereby said flow passage includes said openings and said region.

14. An apparatus as defined in claim 13 wherein said valve body has a third port and said valve element has a third peripheral wall segment for cooperating with the third port to close the third port in the first rotational position and open the third port in the second rotational position at least at one of the first and second axial positions, said third port, when open, communicating with said region between the first and second openings.

15. An apparatus as defined in claim 7 including resilient means for urging the valve element toward the first axial position.

16. An apparatus as defined in claim 7 wherein said valve element has a sloping wall portion which slopes radially inwardly as it extends away from the first port and which cooperates with the housing to define a portion of said flow passage in the second axial position of the valve element.

17. An apparatus comprising:
a valve body having first, second and vent ports;
a generally tubular valve element having a peripheral wall with first, second and vent openings in the peripheral wall leading to the interior of the tubular valve element;
said valve element being mounted in said valve body for rotational movement relative to the valve body between first and second rotational positions and for axial movement relative to the valve body between first and second axial positions;
said second opening and said second port being in communication when the valve element is in said first rotational position and the first axial position;
regions of said valve body and said peripheral wall cooperating to define a restricted passage extending from the first port to the first opening when the valve element is in the first rotational position and the first axial position whereby the restricted passage provides a restriction to flow and restricted flow can occur between the ports;
said valve element when in the first rotational position being movable from the first axial position to the second axial position to eliminate said restriction to flow sufficiently so that flush flow can occur between the first and second ports;
said peripheral wall closing said vent port in said first rotational position and said vent opening communicating with said vent port in the second rotational position to provide communication from the vent port to the interior of the valve element; and
means for resiliently biasing the valve element in a direction from the second axial position to the first axial position.

18. An apparatus as defined in claim 17 including a housing, said housing includes said valve body, and said apparatus includes a pressure transducer in said housing in communication with the interior of the valve element for providing a signal related to the pressure of the fluid in the valve body.

19. An apparatus as defined in claim 17 including an operating handle drivingly coupled to the valve element for manually positioning the valve element, said valve body has a chamber, and said valve element is at least partially in the chamber and has an axial passage which opens into said chamber at one end of the valve element.

* * * * *